(12) United States Patent
Haan et al.

(10) Patent No.: US 8,580,978 B2
(45) Date of Patent: Nov. 12, 2013

(54) PROCESS FOR PREPARING A HYDROXYACID OR HYDROXYESTER

(75) Inventors: Rene Johan Haan, Amsterdam (NL); Jean-Paul Lange, Amsterdam (NL)

(73) Assignee: Shell Oil Company, Houston, TX (US)

( * ) Notice: Subject to any disclaimer, the term of this patent is extended or adjusted under 35 U.S.C. 154(b) by 79 days.

(21) Appl. No.: 12/851,468

(22) Filed: Aug. 5, 2010

(65) Prior Publication Data

US 2011/0046399 A1 Feb. 24, 2011

(30) Foreign Application Priority Data

Aug. 7, 2009 (EP) .................................. 09167506

(51) Int. Cl.
*C07D 307/00* (2006.01)
(52) U.S. Cl.
USPC ....................................................... 549/326
(58) Field of Classification Search
USPC ....................................................... 549/326
See application file for complete search history.

(56) References Cited

U.S. PATENT DOCUMENTS

| | | | |
|---|---|---|---|
| 3,849,457 A | 11/1974 | Haag et al. | 260/413 |
| 3,968,294 A | 7/1976 | Robitschek et al. | 428/213 |
| 4,048,196 A | 9/1977 | Broecker et al. | 260/346.11 |
| 4,301,077 A | 11/1981 | Pesa et al. | 260/346.11 |
| 4,594,130 A | 6/1986 | Chang et al. | 162/16 |
| 4,652,685 A | 3/1987 | Cawse et al. | 568/864 |
| 4,797,382 A | 1/1989 | De Thomas et al. | 502/245 |
| 4,885,411 A | 12/1989 | De Thomas et al. | 568/864 |
| 4,904,342 A | 2/1990 | Arnoldy et al. | 162/76 |
| 5,068,105 A | 11/1991 | Lewis et al. | 424/93 |
| 5,596,113 A | 1/1997 | Douglas et al. | 556/14 |
| 5,608,105 A | 3/1997 | Fitzpatrick | 562/515 |
| 5,614,564 A | 3/1997 | Hwang et al. | 521/84.1 |
| 5,883,266 A | 3/1999 | Elliott et al. | 549/273 |
| 5,892,107 A | 4/1999 | Farone et al. | 562/326 |
| 5,956,964 A | 9/1999 | Wright | 62/304 |
| 6,054,611 A | 4/2000 | Farone et al. | 562/515 |
| 6,152,975 A * | 11/2000 | Elliott et al. | 48/197 R |
| 6,527,914 B1 | 3/2003 | Shevchenko et al. | 162/142 |
| 6,617,464 B2 * | 9/2003 | Manzer | 549/326 |
| 6,894,199 B2 | 5/2005 | Heikkilä et al. | 568/864 |
| 6,946,563 B2 * | 9/2005 | Manzer et al. | 549/326 |
| 2002/0069987 A1 | 6/2002 | Pye | 162/77 |
| 2004/0224902 A1 | 11/2004 | Shukla et al. | 514/22 |
| 2004/0231810 A1 | 11/2004 | Rousu et al. | 162/16 |
| 2005/0221078 A1 | 10/2005 | Lu et al. | 428/326 |
| 2006/0135793 A1 | 6/2006 | Blessing et al. | 549/318 |
| 2006/0162239 A1 | 7/2006 | Van Den Brink et al. | 44/385 |
| 2007/0034345 A1 | 2/2007 | Petrus et al. | 162/72 |
| 2007/0100162 A1 | 5/2007 | Petrus et al. | 562/515 |

FOREIGN PATENT DOCUMENTS

| | | |
|---|---|---|
| DD | 106362 | 6/1974 |
| EP | 69409 | 11/1985 |
| EP | 472474 | 1/1996 |
| EP | 1036878 | 9/2000 |
| GB | 1240580 | 7/1971 |
| GB | 2040275 | 8/1980 |
| JP | 05140323 | 8/1993 |
| JP | 7-18269 | 1/1995 |
| JP | 09059519 | 4/1997 |
| JP | 11029647 | 2/1999 |
| WO | WO8200483 | 2/1982 |
| WO | WO 9826869 | 6/1998 |
| WO | WO 9965851 | 12/1999 |
| WO | WO0159202 | 8/2001 |
| WO | WO 02074760 | 9/2002 |
| WO | WO02085833 | 10/2002 |
| WO | WO03014231 | 2/2003 |
| WO | WO2005058856 | 6/2005 |
| WO | WO2005059016 | 6/2005 |
| WO | WO 2006067171 | 6/2006 |
| WO | WO 2008142127 | 11/2008 |

OTHER PUBLICATIONS

Gary A. Smook, Handbook for Pulp & Paper Technologists, Second Edition, 1992, p. 333.

Michèle Heitz, "Solvent Effects on Liquefaction: Solubilization Profiles of a Canadian Prototype Wood, *Populus deitoids*, in the Presence of Different Solvents," The Canadian Journal of Chemical Engineering, vol. 72 pp. 1021-1027, Dec. 1994.

T. Yamada et al., "Rapid Liquefaction of Lignocellulosic Waste by Using Ethylene Carbonate," Bioresource Technology 70 (1999), pp. 61-67, 1999.

Reid H. Leonard, "Levulinic Acid as a Basic Chemical Raw Material," Newport Industries, Inc., Pensacola, Florida, 48(8) pp. 1331-1341, Aug. 1956.

Kirk-Othmer's Encyclopedia of Chemical Technology, Third Edition, 1981, vol. 13, p. 909.

Ullmann's Encyclopedia of Industrial Chemistry, Fifth Edition, 1990, vol. A15: Isotopes, Natural to Magnesium Compounds, p. 80-81.

Jean-Paul Lange, Valeric Biofuels: A New Family of Cellulosic Biofuels, Angewante 2010.

(Continued)

*Primary Examiner* — Nizal Chandrakumar

(57) ABSTRACT

A process for preparing a hydroxyacid or hydroxyester from a reactant selected from (a) a carboxylic acid having an aldehyde or keto group; and (b) an ester of a carboxylic acid having an aldehyde or keto group;

by contacting the reactant with a metal catalyst in the presence of hydrogen, wherein the metal catalyst is supported on a titanium dioxide or zirconium dioxide support.

17 Claims, No Drawings

(56) References Cited

OTHER PUBLICATIONS

Jesse Q. Bond et al., "Integrated Catalytic Conversion of γ-Valerolactone to Liquid Alkenes for Transportation Fuels," Science, vol. 327, Feb. 26, 2010, pp. 1110-1114.
Jesse Q. Bond et al, Science 2010, Supporting Online Material for *Integrated Catalytic Conversion of γ-Valerolactone to Liquid Alkenes for Transportation Fuels*.

International Search Report for International Application PCT/EP2010/055862 dated Jun. 4, 2010.
European Search Report dated Jun. 2, 2005 for Application No. 0106969.1.
European Search Report dated Jun. 22, 2004 for Application No. 03257858.

* cited by examiner

PROCESS FOR PREPARING A HYDROXYACID OR HYDROXYESTER

TECHNICAL FIELD OF THE INVENTION

The present invention relates to a process for the preparation of a hydroxyacid or hydroxyester.

BACKGROUND OF THE INVENTION

Processes involving catalytic hydrogenation of carboxylic acids or esters thereof having an aldehyde or keto group are known in the art. The hydrogenation of ethyl pyruvate over an alumina-supported platinum catalyst, for example, is described in J. Molecular Catalysis, 49(2), 195-203 (1989).

Levulinic acid can be catalytically hydrogenated to give the corresponding gamma-hydroxy acid 4-hydroxypentanoic acid (known as hydroxyvaleric acid) which subsequently cyclises to form the 5-membered lactone, gammavalerolactone. Early studies reported the hydrogenation of levulinic acid to gammavalerolactone using an unsupported platinum oxide catalyst (J. Am. Chem. Soc, 52, 3010 (1931)).

Other studies have also been reported. In U.S. Pat. No. 5,883,266, for example, the preparation of gammavalerolactone from levulinic acid is described by hydrogenation with a bifunctional metallic catalyst comprising a noble metal, copper, nickel or rhenium, or combinations thereof, optionally on a support which is preferably carbon but which may also be a metal oxide such as alumina or magnesium silicate or combinations thereof. Titania and zirconia supports are mentioned but not exemplified. A preferred catalyst is disclosed to be palladium-rhenium catalyst supported on a carbon support.

The catalytic hydrogenation of levulinic acid to give gammavalerolactone using a metal selected from Group VIII of the Periodic Table, optionally on a catalyst support is also described in WO 02/074760. It is described that a preferred metal catalyst is ruthenium; the support is preferably carbon, $SiO_2$ and $Al_2O_3$, with oxidatively stable carbon being particularly preferred.

Hydrogenation of levulinic acid or its esters to give gammavalerolactone using a hydrogenating metal catalyst on a support is also described in WO 2006/067171. Metal catalysts which are specifically exemplified include rhodium, ruthenium, palladium, nickel and nickel/platinum and rhenium/platinum combinations on a zeolite/silica or silica support.

A significant problem associated with such hydrogenation processes is the susceptibility of the catalyst to poisoning and/or degradation by the acid reactant. Both the transition metal and basic materials in the catalyst support can potentially react with carboxylic acids causing the metal or support to leach or dissolve. Carbon supports overcome the problem of leaching but do not allow for the regeneration of deactivated catalyst by coke burn-off. There therefore remains a need for improved catalyst systems for use in such processes.

Levulinic acid is readily available from cellulose feedstock material and is therefore a convenient starting material for the preparation of gammavalerolactone. Products such as ethyl valerate and pentyl valerate which are obtainable from gammavalerolactone by hydrogenation are of particular interest as fuel components and there therefore remains a particular continuing interest in the development of improved methods for preparing gammavalerolactone from levulinic acid.

SUMMARY OF THE INVENTION

The present invention provides a process for preparing a hydroxyacid or hydroxyester from a reactant selected from (a) a carboxylic acid having an aldehyde or keto group; and
(b) an ester of a carboxylic acid having an aldehyde or keto group;

comprising contacting the reactant with a metal catalyst in the presence of hydrogen, wherein the metal catalyst is supported on a titanium dioxide or zirconium dioxide support.

The present invention is based on the finding that the use of a metal catalyst on a titanium dioxide or zirconium oxide support in the hydrogenation of a carboxylic acid or ester having an aldehyde or keto group to give the corresponding hydroxyacid or hydroxyester affords unexpected improvements in activity, selectivity and/or stability compared to other metal catalysts and supports conventional in the art. Advantageously, the metal catalyst supported on a titanium dioxide or zirconium oxide can selectively hydrogenate the aldehyde or keto group of the carboxylic acid respectively carboxylic ester whilst essentially no hydrogenation of the acid or ester group takes place.

DETAILED DESCRIPTION OF THE INVENTION

In the process of the invention, the reactant may be any carboxylic acid or ester having an aldehyde or keto group.

In one embodiment, the reactant is a carboxylic acid having an aldehyde or keto group.

The reactant is suitably a carboxylic acid or ester of the general molecular formula (I)

$$R^1OOC-(CR^2R^3)_n COR^4 \qquad (I)$$

wherein $R^1$, $R^2$, $R^3$ and $R^4$ are each independently H or a carbon-linked organic group and n is 0 to 40.

Conveniently, the reactant is a compound of formula (I) in which n is 0-3, particularly 2. A carbon-linked organic group is suitably an alkyl group, preferably a C 1-3 alkyl group such as methyl.

In one embodiment, $R^2$ and $R^3$ are each H. In another embodiment, $R^4$ is an alkyl group, preferably a methyl group. $R^1$ is conveniently H or a methyl group.

Where the reactant is a carboxylic acid or ester having a gamma or delta carbonyl group (that is, in the compounds of formula (I) where n is 2 or 3), cyclisation of the resulting hydroxyacid under the conditions of the process of the invention occurs, leading to the formation of 5- or 6-membered lactone products. These lactone products are particularly useful in the preparation of fuel components.

In one particular embodiment, the reactant is levulinic acid (the compound of formula (I) wherein $R^1$, $R^2$ and $R^3$ each are H, $R^4$ is a methyl group and n is 2) or an ester thereof. This reactant may be hydrogenated according to the process of the invention to produce gammavalerolactone.

The metal catalyst for use according to the process of the present invention suitably comprises one or more metals selected from Groups VIIB (group 7), VIII (groups 8-10) and Group IB (group 11) of the Periodic Table of Elements such as platinum, palladium, rhenium, ruthenium, rhodium, osmium, iridium, gold. More preferably the metal catalyst contains at least one metal chosen from the group consisting of platinum, palladium, rhenium, ruthenium, rhodium, osmium, iridium and gold. It will be appreciated that metals other than the aforementioned one or more metals selected from Groups VIIB (group 7), VIII (groups 8-10) and Group IB (group 11) may be present provided that they do not inhibit the catalyst activity.

In one embodiment, the metal catalyst comprises one or more metals selected from platinum, ruthenium, rhodium and iridium.

Conveniently, the metal catalyst comprises a metal selected from platinum, ruthenium, rhodium and iridium in combination with an additional metal selected from rhenium and gold.

In one embodiment, the metal catalyst consists of platinum.

In another embodiment, the metal catalyst consists of ruthenium.

In another embodiment, the catalyst comprises platinum and one or more additional metals selected from Groups VIIB (group 7), VIII (groups 8-10) and Group IB (group 11) of the Periodic Table of Elements. Suitably, the one or more additional metals comprises rhenium, ruthenium, rhodium, iridium, gold. In particular, the catalyst comprises platinum and an additional metal selected from rhenium, iridium and gold.

It will be appreciated that the additional one or more metals may be deposited with the platinum or placed separately on the catalyst support. Where the catalyst comprises one or more different metals in addition to platinum, the one or more additional metal is preferably alloyed to the platinum.

The concentration of metal based on the total weight of the catalyst on its support will typically be in the range of from 0.05 to 5 wt %, suitably from 0.1 to 2 wt %.

Where the catalyst comprises platinum in combination with one or more other metals, the platinum is suitably present in an amount of from 0.05 to 5 wt %, conveniently from 0.1 to 2 wt %.

The support is suitably present in an amount of at least 50 wt %, conveniently at least 95 wt % based on the total weight of metal catalyst on its support.

The present inventors have found that titanium dioxide and zirconium dioxide supported catalysts exhibit improved activity and selectivity in the process of the invention compared to carbon and silica supported catalysts which have previously been described in the literature as being preferred in such hydrogenation processes.

An additional advantage for the titanium dioxide and zirconium oxide supported catalysts of the present invention compared to carbon supported catalysts is that the catalysts of the present invention may be regenerated by means of a coke-burn off procedure whereas carbon supported catalysts cannot survive such a procedure. This represents a significant commercial advantage.

In one embodiment, where the metal catalyst consists of platinum, the support is conveniently titanium dioxide.

In another embodiment, where the metal catalyst comprises platinum and one or more additional metals, this is preferably supported on a zirconium dioxide support.

The temperature at which the process according to the invention is conducted may vary depending on such factors as the metals present in the catalyst and the support used. Preferably the hydrogenation process is performed at a temperature in the range of from 50-350° C., more preferably 150-250° C.

The reactant is suitably contacted with the catalyst at a pressure of 1 to 100 bar (absolute), preferably 2-50 bar.

It will be appreciated that where the reactant is levulinic acid, the pressure, temperature and hydrogen/levulinic acid ratio will conveniently be chosen such that the levulinic acid is in the liquid phase during reaction.

The weight hourly space velocity of the reactant in the process according to the present invention is preferably in the range of from 0.1 to 30 g reactant per g catalyst per hour, more preferably 0.5 to 15 g reactant per g catalyst per hour.

The amount of hydrogen in the process of the invention may suitably be varied between 0.2 and 10 mol hydrogen per mol of reactant to be converted. Preferably, 1-5 mol hydrogen per mol of reactant to be converted is used in the process according to the invention.

The gammavalerolactone product of the process of the invention where the reactant is levulinic acid or an ester thereof may be further hydrogenated to produce valeric acid or transesterified to produce ethyl pentenoate according to the procedures described in WO 2006/067171 and WO 2005/058793. In one embodiment, hydrogenation according to the present invention to produce gammavalerolactone and the subsequent hydrogenation or transesterification steps may suitably be carried out in a single reactor.

In one embodiment, levulinic acid may be upgraded to valeric acid or ethyl pentenoate in a single reactor using a reactive distillation process. In order to manufacture valeric acid, for example, the bottom part of the reactive distillation unit may suitably comprise an levulinic acid hydrogenation catalyst (for example $Pt/TiO_2$) while the upper part suitably comprises a bifunctional catalyst such as the catalysts described in WO 2006/067171. Levulinic acid may be fed in at a suitable location in the reactor, for instance above the bottom part, and hydrogenated to gammavalerolactone using hydrogen fed below the bottom part. Gammavalerolactone vapor entrained with hydrogen then passes over the bifunctional catalyst to be hydrogenated to valeric acid which leaves the reactor at the top together with product water and unconverted hydrogen.

The preparation of ethyl pentenoate by reactive distillation may conveniently be carried out as follows. Levulininc acid may be introduced above the bottom part of a reactor containing the hydrogenation catalyst together with an acidic catalyst (for example $H_2SO_4$ or a solid acid such as a zeolite) chemically or physically mixed to the hydrogenation catalyst and hydrogen and an alcohol (for example methanol or ethanol) are fed below the bottom part. Levulinic acid is hydrogenated to gammavalerolactone over the hydrogenation catalyst and the gammavalerolactone is subsequently transesterified (according to the procedure described in WO 2005/058793, for example) in contact with the alcohol and the acid function. The resulting pentenoate ester is then vaporized and entrained out of the reactor together with unconverted hydrogen, unconverted alcohol and water product.

The latter scheme can be modified to produce alkyl pentanoate in a single step by placing an hydrogenation catalyst in the upper part of the reactor to hydrogenate the vapor of pentenoate ester into pentanoate ester using unconverted hydrogen.

Throughout the description and claims of this specification, the words "comprise" and "contain" and variations of the words, for example "comprising" and "comprises", mean "including but not limited to", and do not exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Preferred features of each aspect of the invention may be as described in connection with any of the other aspects.

Other features of the present invention will become apparent from the following examples. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith.

Moreover unless stated otherwise, any feature disclosed herein may be replaced by an alternative feature serving the same or a similar purpose.

EXAMPLES

The invention will now be further illustrated by means of the following non-limiting examples which investigate the advantages of a process according to the present invention compared to analogous catalytic hydrogenations known in the art.

Example 1

Levulinic acid (LA) was catalytically hydrogenated using a process according to the present invention. The catalysts used were 1 wt % Pt on $TiO_2$; 0.5 wt % Pt and 0.5 wt % Re on $TiO_2$; 0.5 wt % Pt and 0.5 wt % Au on $TiO_2$, 0.5 wt % Pt and 0.5 wt % Ru on $TiO_2$; 0.5 wt % Pt and 0.5 wt % Ir on $TiO_2$; 0.5 wt % Pt and 0.5 wt % Re on $ZrO_2$; 0.5 wt % Pt and 0.5 wt % Au on $ZrO_2$; 1 wt % Pd on $ZrO_2$; 3 wt % Pd on $ZrO_2$.

Catalysts were prepared using an incipient wetness impregnation procedure. Before impregnation, the supports were pre-dried at 300° C. for 1 hour. The required amount of metal solution was calculated and prepared based on the pore volumes of the supports and the desired metal loading such that the total volume of the solution for impregnation was enough to fill 95%+/−5% of the support pores. The supports used, which are commercially available, have the properties outlined in Table 1 below:

TABLE 1 properties of catalyst supports

| Support | BET [m²/g] | V pore [mL/g] | Obtained from |
|---|---|---|---|
| $SiO_2$ | 317.9 | 0.788 | Engelhard (currently BASF) |
| $TiO_2$ | 44.2 | 0.300 | P25 (95% Anatase) from Degussa |
| $ZrO_2$ | 55.5 | 0.320 | Johnson Matthey | a - all supports were extruded by Criterion

The following metal salts were used for catalyst preparation: 5th-row metals: $Ru(NO)(NO_3)_3$, $RhCl_3.3(H_2O)$, $(NH_4)_4PdCl_2$; 6th-row metals: $NH_4ReO_4$, $IrCl_4$, $(NH_4)_2PtCl_4$, $H_2Cl_4Au.3(H_2O)$.

The catalysts were dried for 4 h at 120° C. and calcined for 2 h at 450° C.

As a comparison, the same process was repeated but using as the catalysts 1.12 wt % Pt on $SiO_2$ (from CRI), 0.5 wt % Pt and 0.5 wt % Re on $SiO_2$, 1 wt % Pt on activated carbon (from Evonik), 1 wt % Pd on carbon (from Acros).

The experiments were carried out using a four-barrel microflow unit consisting of 4 parallel Hastelloy HC 276 reactors (1 cm ID) with an isothermal zone of 25 cm and an internal volume of 30 mL. The reactors can be operated between 40 and 500° C. under 1.5 to 80 bar pressure. The liquid feed was fed to the reactor by a 1000 mL ISCO 1000D pump with a maximum flow rate of 50 mL/h. The hydrogen was applied to the reactor through a mass flow controller with a maximum flow rate of 50 NL/h.

The catalysts were loaded as crushed (30-80 mesh) particles and diluted in an equal weight of SiC (0.2 mm). The reduction was carried at atmospheric pressure at 10 NL/h (typically GHSV 2000-5000 mL/g/h) for 3 h at 300° C. After reduction the temperature was lowered to the desired reaction temperature under target $H_2$ flow and pressure and the LA flow was admitted to the reactor.

Tests were carried out at 200° C. and 40 bar $H_2$ with LA (89 wt %), optionally containing gammavalerolactone (GVL) 11 wt %, at a weight hourly space velocity (WHSV) of 0.5-15 g/g/h and a constant $H_2$/LA molar ratio of 5 in the feed. Runs were carried out at one or two WHSVs.

The % conversion of the LA was monitored, providing an indication of the stability of catalyst activity. Also monitored was the percentage of the desired reaction product gammavalerolactone (GVL) as an indicator of catalyst selectivity. Catalyst activity was evaluated and expressed in terms of the pseudo 1st order rate constant $k_1$, which was calculated from the LA conversion X and feed space velocity WHSV according to the following equation:

$$k_1 = -\ln(1-X) \cdot WHSV$$

It should be noted that $k_1$ contains the contribution of $H_2$ partial pressure to the kinetics. This contribution can be assumed to be identical for all runs and constant within the run due to the molar excess of $H_2$ fed.

The stability and selectivity results are summarized in Tables 2 and 3 below. The numbers reported in the tables represent the metal loading in wt %.

TABLE 2

| TOS H | WHSV g/g/h | LA conversion mol% | GVL selectivity mol % | $k_1$ g/g/h |
|---|---|---|---|---|
| $TiO_2$ | | | | |
| | | 1 Pt/$TiO_2$ | | |
| 10 | 9.0 | 95.5 | 96.3 | 27.9 |
| 50 | 9.0 | 92.7 | 99.4 | 23.6 |
| 110 | 9.0 | 85.9 | 96.6 | 17.6 |
| | | 0.5 Pt 0.5 Re/$TiO_2$ | | |
| 10 | 9.0 | 77.8 | 102.5 | 13.5 |
| 50 | 9.0 | 61.3 | 98.9 | 8.5 |
| 110 | 9.0 | 50.0 | 102.7 | 6.2 |
| | | 0.5 Pt 0.5 Au/$TiO_2$ | | |
| 10 | 9.0 | 73.3 | 93.8 | 11.9 |
| 50 | 9.0 | 53.3 | 100.8 | 6.8 |
| 110 | 9.0 | 35.2 | 112.4 | 3.9 |
| | | 0.5 Pt 0.5 Ru/$TiO_2$ | | |
| 10 | 12.4 | 54.1 | 99.2 | 9.7 |
| 45 | 12.4 | 40.5 | 92.1 | 6.4 |
| 102 | 12.3 | 24.9 | 101.8 | 3.5 |
| | | 0.5 Pt 0.5 Ir/$TiO_2$ | | |
| 10 | 5.7 | 81.7 | 94.8 | 9.7 |
| 51 | 5.7 | 76.9 | 99.6 | 8.4 |
| 110 | 5.7 | 16.8 | 98.5 | 1.1 |
| | | 3 Pd/$TiO_2$ | | |
| 10 | 2.2 | 38.9 | 34.8 | 1.1 |
| 51 | 0.6 | 55.1 | 28.5 | 0.4 |
| | | 0.5 Pd 0.5 Au/$TiO_2$ | | |
| 10 | 4.5 | 14.6 | 39.5 | 0.7 |
| 45 | 4.5 | 12.1 | 54.5 | 0.6 |
| | | 1 Ir/$TiO_2$ | | |
| $TiO_2$ | | | | |
| 10 | 4.49 | 34.8 | 100 | 1.92 |
| 51 | 4.49 | 23.2 | 94 | 1.19 |

TABLE 2-continued

| TOS H | WHSV g/g/h | LA conversion mol% | GVL selectivity mol % | $k_1$ g/g/h |
|---|---|---|---|---|
| ZrO$_2$ | | | | |
| | | 0.5 Pt 0.5 Re/ZrO$_2$ | | |
| 10 | 4.5 | 86.1 | 93.1 | 8.9 |
| 45 | 4.5 | 81.6 | 99.1 | 7.6 |
| 86 | 4.5 | 73.5 | 102.8 | 6.0 |
| | | 1 Pd/ZrO$_2$ | | |
| 10 | 2.2 | 25.6 | 33.5 | 0.7 |
| 51 | 0.6 | 36.3 | 44.0 | 0.3 |
| 111 | 0.6 | 41.9 | 38.0 | 0.3 |
| | | 0.5 Pt 0.5 Au/ZrO$_2$ | | |
| 10 | 4.5 | 86.1 | 93.1 | 8.9 |
| 45 | 4.5 | 81.6 | 99.1 | 7.6 |
| 86 | 4.5 | 73.5 | 102.8 | 6.0 |

TABLE 3

| Comparative examples TOS h | WHSV g/g/h | LA conversion mol% | GVL selectivity mol% | $k_1$ g/g/h |
|---|---|---|---|---|
| SiO$_2$ | | | | |
| | | 1.12 Pt/SiO$_2$ | | |
| 12 | 2.0 | 71.2 | 93.1 | 2.5 |
| 56 | 0.6 | 92.7 | 93.4 | 1.5 |
| 110 | 0.6 | 89.5 | 91.6 | 1.3 |
| | | 0.5 Pt 0.5 Re/SiO$_2$ | | |
| 10 | 13.5 | 11.7 | 52.4 | 1.7 |
| 54 | 13.5 | 3.0 | 126.1 | 0.4 |
| 102 | 13.4 | 4.1 | 68.4 | 0.6 |
| C | | | | |
| 10 | 10.2 | 49.4 | 79.9 | 6.9 |
| 54 | 10.2 | 28.3 | 78.1 | 3.4 |
| 102 | 10.1 | 20.6 | 81.6 | 2.3 |
| | | 1% Pd on carbon | | |
| 10 | 2.2 | 13.6 | 86 | 0.3 |
| 51 | 0.6 | 31.3 | 61 | 0.2 |
| 111 | 0.6 | 38.9 | 43 | 0.3 |

(TOS is time on stream)

From the results presented in Tables 2 and 3, it can be seen that the titanium dioxide and zirconium dioxide supported catalysts according to the present invention are advantageous in terms of activity ($k_1$) compared to silica and carbon supported catalysts. The platinum containing catalysts in particular appear to show good activity ($k_1$) and selectivity and improved long-term activity. Of particular note is Pt/TiO$_2$, which not only exhibits good selectivity but is also active over an extended time period, losing less than 50% of its initial activity ($k_1$) over a time period of 110 hours.

Example 2

The suitability of various support materials for use with carboxylic acid reactants was assessed by subjecting them to a leaching test involving cooking 1 g of various support materials shaped as extrudates for approximately one week in 10 g of liquid valeric acid at 150° C. Following this test, catalyst integrity was inspected visually and an element analysis of the liquid phase was performed to establish whether there had been material leaching.

Results are presented in Table 4 below. From these results it can be seen that TiO$_2$ and ZrO$_2$ survive the leaching test well with minimal metal leaching, indicating that they are sufficiently robust to be useful in a practical catalytic system. Many of the various other support materials tested showed substantial degradation under the same conditions, for example the ultra stable Y zeolite showed an exceptionally high leaching rate of aluminium. Other oxides, for example Sn, W, Mg also exhibited significant decomposition.

TABLE 4

| Material | [Si/ppm] | [M/ppm] | M |
|---|---|---|---|
| Zeolites | | | |
| USY/SlO$_2$ | 5.6 | 31 | Al |
| H-Beta/Al$_2$O$_3$ | 0.6 | 0 | Al |
| H-ZSM-5/SiO$_2$ | 2 | 2.7 | Al |
| Pt/ZSM/ SiO$_2$ | 33.9 | 8.6 | Al |
| Pt/ZSM/ SiO$_2$ | 1.6 | 15.6 | Al |
| Amorphous Silica-Alumina | | | |
| ASA (X600 from CRI) ** | | catalyst dissolved | |
| ASA (MS13/110W ASA from Grace Davison) * | <0.5 | 3245 | Al |
| ASA (ph swing, TC = 500° C.) | 8.2 | 1.9 | Al |
| ASA (ph swing, TC = 700° C.) | 48.5 | 13.3 | Al |
| Alumina | | | |
| Gamma-Al$_2$O$_3$ | | particle dissolved | |
| Theta-alumina | | particle dissolved | |
| Alpha-alumina | | 24 | Al |
| Titanium Oxide | | | |
| TiO$_2$ | 0 | 0 | Ti |
| TiO$_2$ Criterion Kataleuna | 6.7 | <0.5 | Ti |
| TiO$_2$ SiO$_2$ PQ | 76.6 | 3.1 | Ti |
| TiO$_2$ SiO$_2$ Grace | 30.2 | <0.5 | Ti |
| Zirconium Oxide | | | |
| ZrO$_2$ | | 0.8 | Zr |
| ZrO$_2$ | | 8.8 | Zr |
| Other materials | | | |
| Sn/Sb/SiO$_2$ | 1.1 | <1/14 | Sn/Sb |
| Sn/Zr/SiO$_2$ | 56.5 | 81.5/440 | Sn/Zr |
| Tungstosilicic acid hydrate | 34.5 | 120 | W |
| Tungstophosphoric acid hydrate | 675 | 1720 | W |
| MgO | 0 | 304 | Mg |
| CaO | | catalyst dissolved | |

\* tested in liquid levulinic acid instead of liquid valeric acid.
\*\* tested in both liquid levulinic acid and liquid valeric acid.

What is claimed is:

1. A process for preparing a 5- or 6-member lactone product comprising:
   providing a metal catalyst comprising a titanium dioxide or zirconium dioxide support in a reactor; wherein the metal catalyst comprises a metal of any one of groups 7-11 or a combination of two or more such metals;
   providing the reactor with a hydrogen flow; and
   providing the reactor with a reactant flow comprising a reactant of a carboxylic acid or an ester of a carboxylic acid of the general molecular formula (I)

$$R^1OOC\text{---}(CR^2R^3)_nCOR^4 \tag{I}$$

wherein $R^1$, $R^2$, $R^3$, and $R^4$ each comprises a hydrogen or a an alkyl group and n is 2 or 3;
   wherein the reactant flow is provided at a weight hourly space velocity in the range of from 0.1 to 30 grams of reactant per gram of catalyst per hour;

wherein contact of at least a portion of the reactant with the metal catalyst in the reactor in the presence of hydrogen produces a reaction product comprising a 5- or 6-member lactone product.

2. The process of claim 1 wherein the reactant is a carboxylic acid having a gamma carbonyl group.

3. The process of claim 1 wherein the reactant is levulinic acid and the product of the process is gammavalerolactone.

4. The process of claim 1 wherein the metal catalyst comprises platinum or ruthenium.

5. The process of claim 1 wherein the metal catalyst comprises platinum in combination with rhenium, ruthenium, iridium or gold.

6. The process of claim 1 wherein the reactant is contacted with the catalyst at a temperature of from 50° C. to 350° C.

7. The process of claim 3 wherein levulinic acid is hydrogenated to gammavalerolactone and subsequently further hydrogenated to give valeric acid or transesterified to give ethyl pentenoate in a single vessel that operates under a reactive distillation condition.

8. The process of claim 4 wherein the metal catalyst comprises platinum in combination with rhenium, ruthenium, iridium or gold.

9. The process of claim 1 wherein the reactant is contacted with the catalyst at a pressure of from 2 to 50 bar (absolute).

10. The process of claim 9 wherein the metal catalyst comprises platinum in combination with rhenium, ruthenium, iridium or gold.

11. The process of claim 10 wherein the reactant is levulinic acid and the product of the process is gammavalerolactone.

12. The process of claim 11 wherein levulinic acid is hydrogenated to gammavalerolactone and subsequently further hydrogenated to give valeric acid or transesterified to give ethyl pentenoate in a single vessel that operates under a reactive distillation condition.

13. The process of claim 1 wherein the weight hourly space velocity in the range of from 0.5 to 15 grams reactant per gram of catalyst per hour.

14. The process of claim 1 wherein the hydrogen flow and reactant flow are provided at a ratio in a range of from 0.2 and 10 mol of hydrogen per mol of reactant to be converted.

15. The process of claim 14 wherein the ratio is in a range of from 1 and 5 mol of hydrogen per mol of reactant to be converted.

16. The process of claim 6 wherein the reactant is contacted with the catalyst at a temperature of from 150° C. to 250° C.

17. The process of claim 1 wherein the hydrogen flow and the reactant flow are provided at different flow rates.

* * * * *